United States Patent
Hsieh et al.

(10) Patent No.: US 12,422,311 B2
(45) Date of Patent: Sep. 23, 2025

(54) MULTI-ZONE TEMPERATURE CONTROL DEVICE AND MULTI-ZONE TEMPERATURE CONTROL METHOD

(71) Applicant: DELTA ELECTRONICS, INC., Taoyuan (TW)

(72) Inventors: Ming-Che Hsieh, Taoyuan (TW); Yu-Kai Kao, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 606 days.

(21) Appl. No.: 17/871,739

(22) Filed: Jul. 22, 2022

(65) Prior Publication Data
US 2023/0366753 A1     Nov. 16, 2023

(30) Foreign Application Priority Data

May 12, 2022   (CN) .......................... 202210517681.3

(51) Int. Cl.
*B01L 7/00*    (2006.01)
*A61B 1/04*    (2006.01)
(Continued)

(52) U.S. Cl.
CPC .......... *G01K 11/3213* (2013.01); *A61B 1/043* (2013.01); *B01L 7/52* (2013.01); *C12M 1/38* (2013.01); *B01L 2300/1805* (2013.01)

(58) Field of Classification Search
CPC .. G05D 23/1932; G05D 23/1934; C12M 1/38
See application file for complete search history.

(56) References Cited

U.S. PATENT DOCUMENTS 3,556,731 A * 1/1971 Martin ...................... C12M 1/26
                                                        422/65
6,558,947 B1 * 5/2003 Lund ........................ B01L 7/54
                                                        435/303.1
(Continued)

FOREIGN PATENT DOCUMENTS

CN    110736683 A    1/2020
CN    114018976 A    2/2022
(Continued)

OTHER PUBLICATIONS

Office Action dated Jun. 21, 2023 of the corresponding Taiwan patent application No. 111117782.

*Primary Examiner* — Jerry-Daryl Fletcher
*Assistant Examiner* — Daniel C Comings
(74) *Attorney, Agent, or Firm* — HDLS IPR SERVICES; Chun-Ming Shih

(57) ABSTRACT

A multi-zone temperature control device has multiple thermo-conductive reservoirs for accommodating a specimen, multiple temperature adjustment devices for adjusting temperatures of multiple adjustment blocks, a driving device, and a control device. The control device executes multiple temperature control procedures at the same time. During the execution of each temperature control procedure, the present disclosure makes the adjustment blocks contact and leave the thermo-conductive reservoirs in the same zone, such that the thermo-conductive reservoirs reach the target temperatures of the temperature control procedure sequentially.

18 Claims, 11 Drawing Sheets

(51) Int. Cl.
*C12M 1/38* (2006.01)
*G01K 11/3213* (2021.01)

(56) References Cited

U.S. PATENT DOCUMENTS

| | | | |
|---|---|---|---|
| 6,767,512 B1 * | 7/2004 | Lurz | B01L 7/54 |
| | | | 436/155 |
| 7,799,521 B2 * | 9/2010 | Chen | G01N 35/00009 |
| | | | 435/303.1 |
| 2011/0312102 A1 * | 12/2011 | Jo | G01J 3/0216 |
| | | | 436/164 |
| 2012/0095116 A1 * | 4/2012 | Kishi | C12N 9/506 |
| | | | 435/5 |
| 2012/0308990 A1 * | 12/2012 | TerMaat | B01L 7/52 |
| | | | 435/3 |
| 2017/0333905 A1 | 11/2017 | Fuhr et al. | |
| 2021/0060548 A1 | 3/2021 | Higgins et al. | |

FOREIGN PATENT DOCUMENTS

| | | | | |
|---|---|---|---|---|
| JP | WO2009035061 A1 * | 12/2010 | | B01L 3/50273 |
| WO | 2016091344 A2 | 6/2016 | | |

* cited by examiner

MULTI-ZONE TEMPERATURE CONTROL DEVICE AND MULTI-ZONE TEMPERATURE CONTROL METHOD

BACKGROUND OF THE DISCLOSURE

Technical Field

The disclosure relates to a temperature control device and a temperature control method, particularly relates to a multi-zone temperature control device and a multi-zone temperature control method.

Description of Related Art

In the present biological inspection device, in order to accelerate the self-replication of the biological specimen, the biological specimen needs to reach multiple designated temperatures sequentially.

For example, in the polymerase chain reaction (PCR), the biological specimen needs to be heated and cooled repeatedly to make the biological specimen reach the required temperature of denaturing, annealing, and extending sequentially, thereby achieving the purpose of replicating DNA.

However, the related-art biological inspection device may only execute one temperature control procedure at the same time. Further, during executing the temperature control procedure, the idle inspection position of no biological specimen being disposed is not usable, and thus the inspection efficiency is harmed.

On the other hand, if the temperature control procedure is executed only after all the inspection positions are filled with the biological specimens for achieving the maximal inspection efficiency, the waiting time for inspection is greatly increased.

In view of this, the inventors have devoted themselves to the aforementioned related art, researched intensively try to solve the aforementioned problems.

SUMMARY OF THE DISCLOSURE

The purpose of the disclosure is to provide a multi-zone temperature control device and a multi-zone temperature control method, which may independently perform the temperature control to a plurality of zones. In some embodiments, a multi-zone temperature control device is disclosed. The multi-zone temperature control device includes a receiver device, a plurality of temperature adjustment devices, a driving device, and a control device. The receiver device includes a plurality of thermo-conductive reservoirs configured to accommodate a specimen. At least one of the thermo-conductive reservoirs belongs to a first zone and at least another one of the thermo-conductive reservoirs belongs to a second zone. The temperature adjustment devices are configured to adjust temperatures of a plurality of adjustment blocks, and contact the thermo-conductive reservoirs through the adjustment blocks to adjust temperatures of the thermo-conductive reservoirs. The driving device is configured to change a contact status between the adjustment blocks and the thermo-conductive reservoirs. The control device is electrically connected with the driving device and the temperature adjustment devices, and configured to execute a first temperature control procedure to control at least one of the temperature adjustment devices to adjust temperature, and control the driving device to change the contact status between at least one of the adjustment block and the thermo-conductive reservoir in the first zone to make the thermo-conductive reservoir in the first zone reach a plurality of target temperatures of the first temperature control procedure sequentially, and configured to execute a second temperature control procedure to control at least another one of the temperature adjustment devices to adjust temperature, and control the driving device to change the contact status between at least another one of the adjustment block and the thermo-conductive reservoir in the second zone to make the thermo-conductive reservoir in the second zone reach a plurality of target temperatures of the second temperature control procedure sequentially.

In some embodiments, a multi-zone temperature control method is disclosed. The method includes: a) executing a first temperature control procedure to control a first temperature adjustment device to adjust temperature of a first adjustment block, and control a driving device to adjust a first contact status between the first adjustment block and a first thermo-conductive reservoir to make the first thermo-conductive reservoir reach a plurality of target temperatures of the first temperature control procedure sequentially; and b) at the same time of executing the first temperature control procedure, executing a second temperature control procedure to control a second temperature adjustment device to adjust temperature of a second adjustment block, and control the driving device to adjust a second contact status between the second adjustment block and a second thermo-conductive reservoir to make the second thermo-conductive reservoir reach a plurality of target temperatures of the second temperature control procedure sequentially.

The disclosure may be used to perform temperature change control to multiple groups of specimens simultaneously.

DETAILED DESCRIPTION

The technical contents of this disclosure will become apparent with the detailed description of embodiments accompanied with the illustration of related drawings as follows. It is intended that the embodiments and drawings disclosed herein are to be considered illustrative rather than restrictive.

The disclosure provides a multi-zone temperature control device and a multi-zone temperature control method, which may automatically execute the heating/cooling process in the biological inspection (or bioassay).

Specifically, the disclosure may rapidly change the temperature of the biological specimen through contact-type heating/cooling, and further achieve precise temperature adjustment control.

Figure 1:
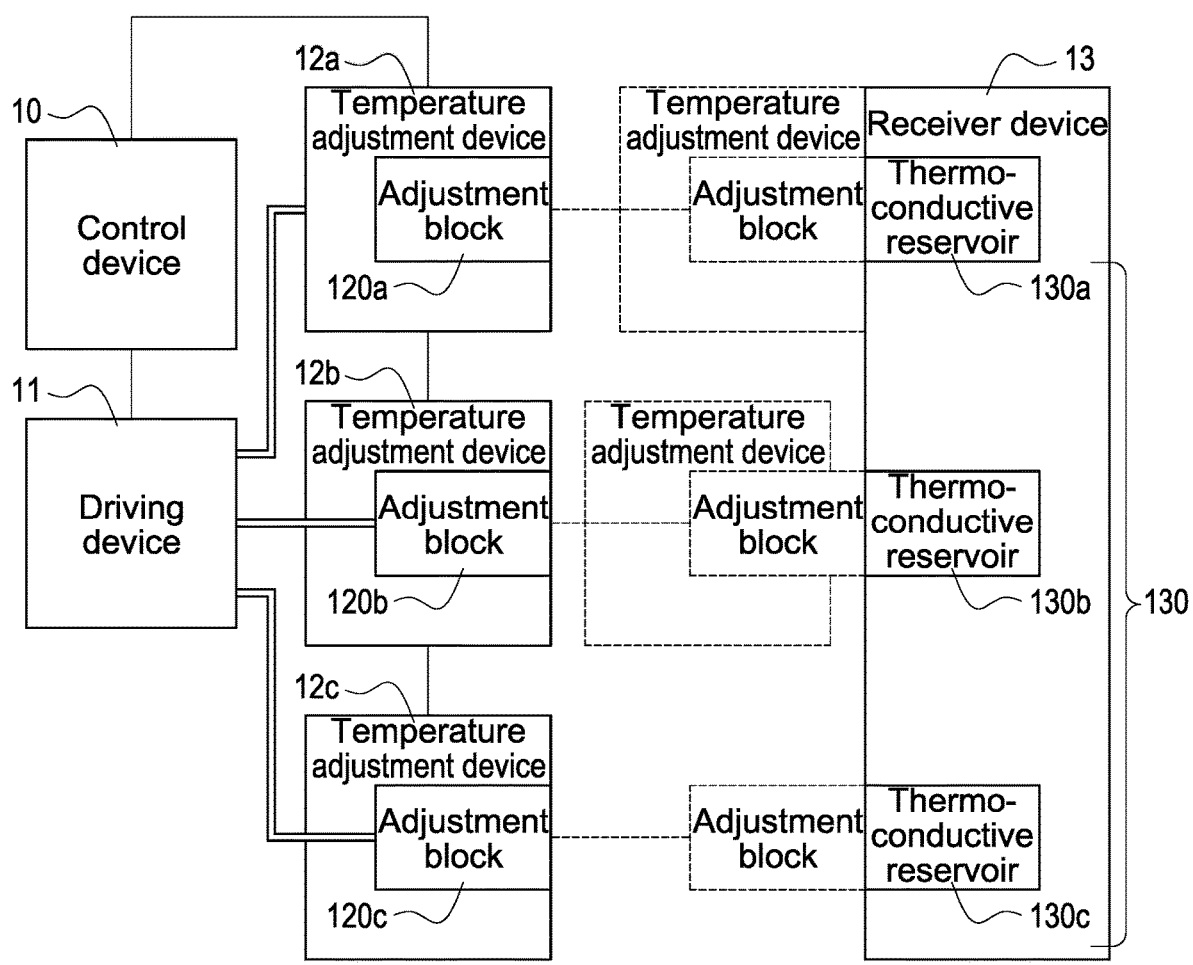
FIG. 1 is an architecture diagram of a multi-zone temperature control device of the disclosure in accordance with some embodiments.
Figure 2:
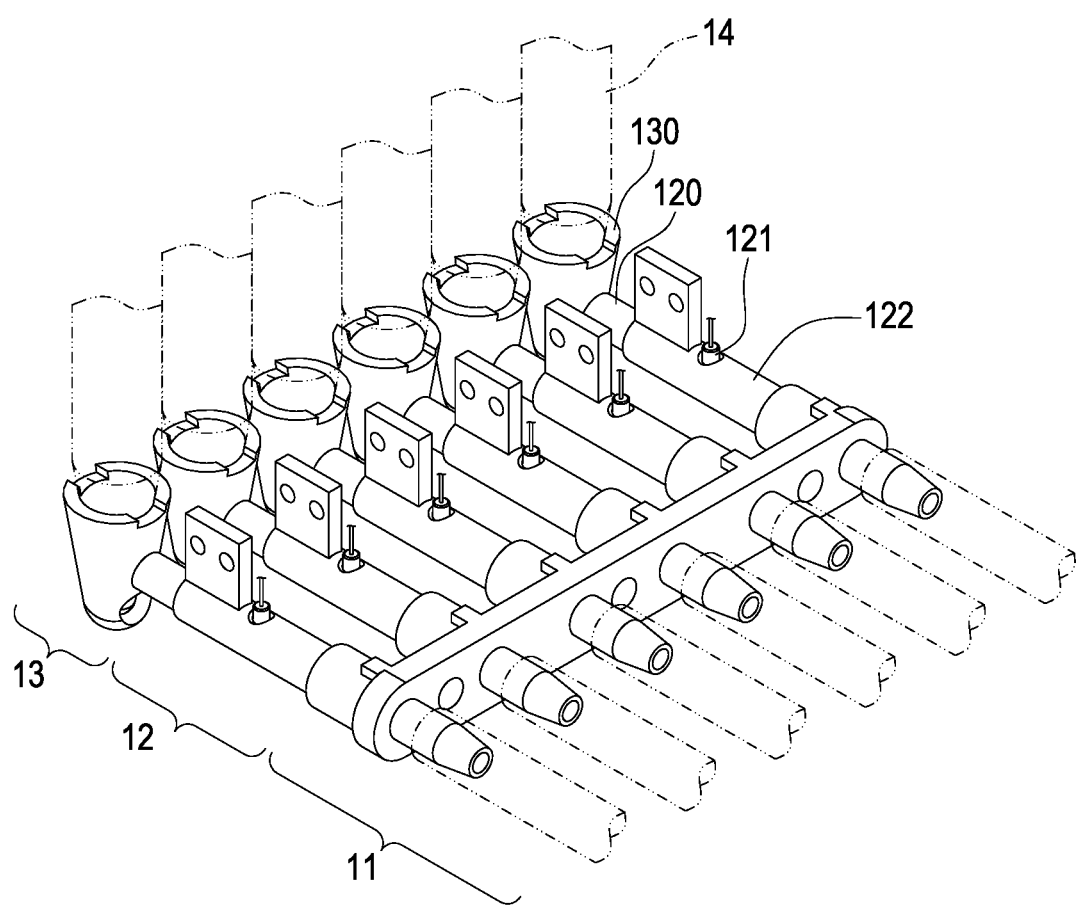
FIG. 2 is a schematic diagram of partial exterior of the multi-zone temperature control device of the disclosure in accordance with some embodiments.
Figure 4:
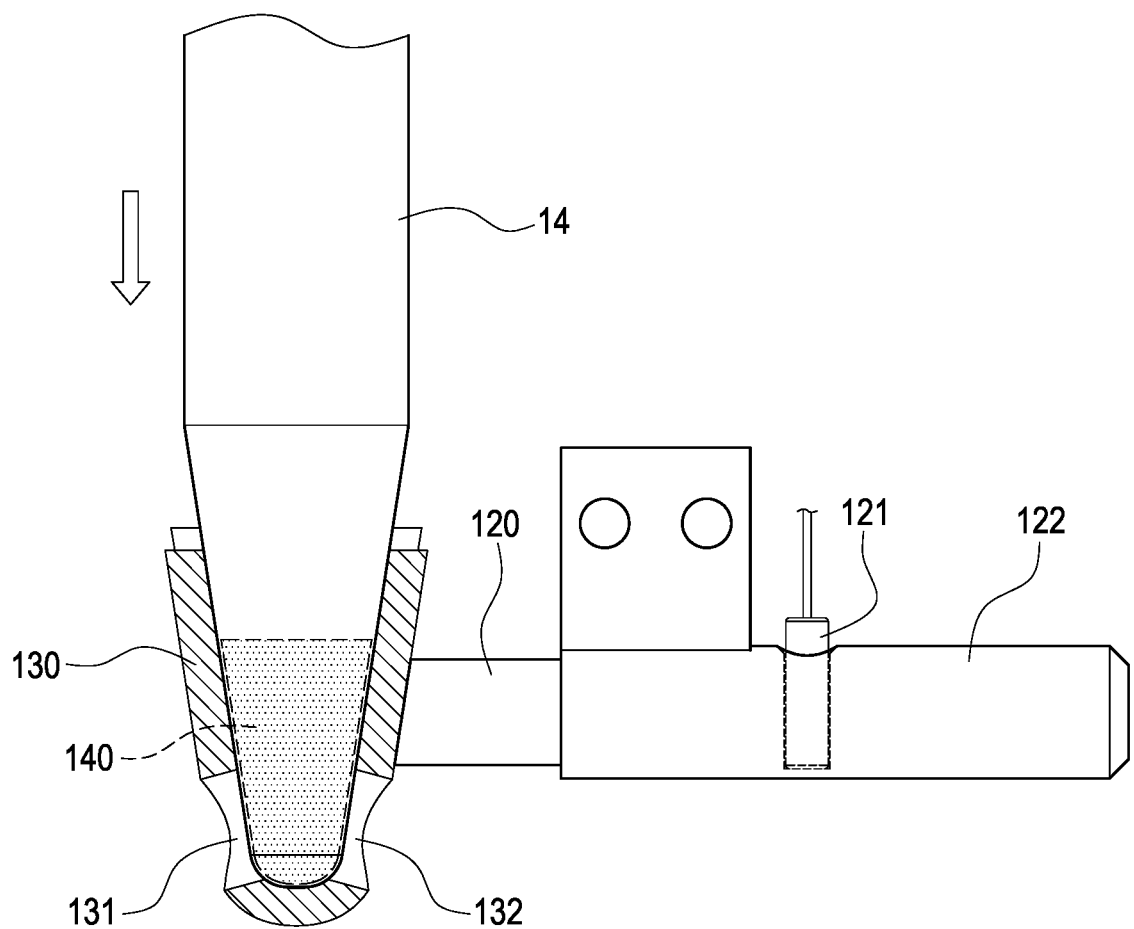
FIG. 4 is a heating schematic diagram of the multi-zone temperature control device of the disclosure in accordance with some embodiments.

Please refer to FIG. 1, FIG. 2, and FIG. 4, FIG. 1 is an architecture diagram of a multi-zone temperature control device of the disclosure in accordance with some embodiments, FIG. 2 is a schematic diagram of partial exterior of the multi-zone temperature control device of the disclosure in accordance with some embodiments, and FIG. 4 is a heating schematic diagram of the multi-zone temperature control device of the disclosure in accordance with some embodiments.

The multi-zone temperature control device 1 of the embodiment includes a control device 10, a driving device 11, a plurality of temperature adjustment devices 12 (three temperature adjustment devices 12a-12c are shown in FIG. 1 as an example) and a receiver device 13.

The receiver device 13 may include a plurality of thermo-conductive reservoirs 130 (three thermo-conductive reservoirs 130a-130c are shown in FIG. 1 as an example). The thermo-conductive reservoirs 130 are used to accommodate a plurality of groups of specimens 140.

Specifically, the inspector may respectively put multiple groups of specimens 140 into multiple test tubes 14 (for example, plastic test tube), and respectively put the test tubes 14 into multiple thermo-conductive reservoirs 130. In the disclosure, the test tube 14 may be all kinds of reagent container or biological specimen container, here is not intended to be limiting.

In the disclosure, the temperature of the thermo-conductive reservoir 130 is being adjusted through using heated/cooled adjustment block to contact the thermo-conductive reservoir 130, and the temperature of the test tube 14 in the thermo-conductive reservoir 130 is indirectly being adjusted, and the temperature of the specimen 140 is further being adjusted.

In some embodiments, the thermo-conductive reservoir 130 may completely cover a part (for example, head portion) of the test tube 14. The adjustment block 120 is used to adjust the temperature of the thermo-conductive reservoir 130 by directly contacting the thermo-conductive reservoir 130, and indirectly adjust the temperature of the test tube 14 disposed in the thermo-conductive reservoir 130.

In some embodiments, the thermo-conductive reservoir 130 has opening disposed thereon, the adjustment block 120 may be inserted into the thermo-conductive reservoir 130 through the opening to simultaneously contact the thermo-conductive reservoir 130 and the test tube 14 disposed in the thermo-conductive reservoir 130. As a result, the adjustment block 120 may directly and simultaneously adjust the temperature of the thermo-conductive reservoir 130 and the temperature of the test tube 14.

In the disclosure, the thermo-conductive reservoirs 130 may be divided into a plurality of zones according to inspection requirements. One or multiple thermo-conductive reservoirs 130 belong to the same zone are being executed with the same temperature control procedures. That is, one or multiple groups of specimens in the same zone are being controlled under the same stage of the same temperature or the same temperature cycle.

In some embodiments, the thermo-conductive reservoir 130 may be a metal cup with high-thermal conductivity, for example, the metal with the thermal conductivity which is greater than or equal to 200 W/m*K.

In some embodiments, the thermo-conductive reservoir 130 may be a metal thin cup, for example, the thickness is less than or equal to 0.5 mm.

The temperature adjustment devices are used to adjust the temperatures of the adjustment blocks 120. The disclosure may be used to adjust the temperature of the thermo-conductive reservoir 130 by moving the adjustment block 120, which has temperature being adjusted, to contact the thermo-conductive reservoir 130.

In some embodiments, each temperature adjustment device 12 may include one or multiple thermostats 121. The thermostat 121 may be a heater or a cryostat, for example, electric heater or thermoelectric cooling chip, and used to heat or cool the corresponding adjustment block 120.

The driving device 11 is used to change the contact statuses between the adjustment blocks 120 and the thermo-conductive reservoirs 130.

Specifically, the driving device 11 may make the adjustment block 120 contact or leave the thermo-conductive reservoir 130 through moving the position of each adjustment block 120 by the movable component 122.

In some embodiments, the movable component 122 may have a telescoping structure or a rotational structure, and is configured to move the connected adjustment block 120 through the telescoping structure or the rotational structure.

In some embodiments, the driving device 11 is a motor power device, and is configured to move the adjustment block 120 through the movable component 122 such as motor, transmission part, etc.

In some embodiments, the driving device 11 is a pneumatic power device, and is configured to move the adjustment block 120 through the movable component 122 such as pneumatic driver, gas pipeline, etc.

In some embodiments, for the temperature adjustment device (or thermoregulator) 12a as shown in FIG. 1, the driving device 11 may simultaneously move the temperature adjustment device 12a (including thermostat 121) and the adjustment block 120a thereof to the receiver device 13 to make the adjustment block 120a contact the thermo-conductive reservoir 130a.

In some embodiments, for the temperature adjustment device (or thermoregulator) 12b as shown in FIG. 1, the driving device 11 may simultaneously move the temperature adjustment device 12b (including thermostat 121) and the adjustment block 120b thereof, and only the adjustment block 120b moves to reach the receiver device 13 and contact the thermo-conductive reservoir 130b.

In the aforementioned two embodiments, when the adjustment blocks 120a, 120b contact the thermo-conductive reservoirs 130a, 130b, the temperature adjustment devices 12a, 12b may continuously perform temperature adjustment to the adjustment blocks 120a, 120b to increase the temperature adjustment efficiency.

In some embodiments, for the temperature adjustment device (or thermoregulator) 12c as shown in FIG. 1, the driving device 11 may only move the adjustment block 120c (without thermostat 121) to the thermo-conductive reservoir 130c. As a result, since only the adjustment block 120c with smaller volume contacts the thermo-conductive reservoir 130c, the distance between the thermo-conductive reservoirs 130 in the receiver device 13 may be reduced for accommodating more thermo-conductive reservoirs 130 or reducing the volume of the multi-zone temperature control device 1.

The control device 10 may include a microcontroller unit (MCU), a central processing unit (CPU), a field-programmable gate array (FPGA), a system on a chip (SoC), or the other types of control circuit. The control device 10 is electrically connected to the driving device 11 and the temperature adjustment device 12, and used to control the multi-zone temperature control device 1 to respectively execute corresponding temperature control procedures to the thermo-conductive reservoirs 130 in multi-zone.

In some embodiments, when the thermo-conductive reservoir 130 is divided into more than two zones, the control device 10 may simultaneously execute the first temperature control procedure to all the thermo-conductive reservoirs 130 in the first zone to make the thermo-conductive reservoirs 130 in the first zone sequentially reach multiple target temperatures required by the first temperature control procedure, and simultaneously execute the second temperature control procedure to all the thermo-conductive reservoirs 130 in the second zone to make the thermo-conductive reservoirs 130 in the second zone sequentially reach multiple target temperatures required by the second temperature control procedure.

In some embodiments, the first temperature control procedure and the second temperature control procedure may be the same temperature control procedure, and have the target temperatures with the same values and the same sequence. The difference between the first temperature control procedure and the second temperature control procedure is that the execution time point is different.

For example, if the required time for executing the temperature control procedure is greater than 30 minutes (for example, 120 minutes), the multi-zone temperature control device 1 may execute the first temperature control procedure to the first zone, and begin to execute the second temperature control procedure (new inspection) to the second zone after 30 minutes.

As a result, if the receiver device 13 has idle thermo-conductive reservoir 130, the multi-zone temperature control device 1 may be configured to begin a new inspection without waiting for completion of previous temperature control procedure.

Please refer to FIG. 1, for example, the inspector may set the thermo-conductive reservoir 130a and the thermo-conductive reservoir 130b to be the first zone, and set the thermo-conductive reservoir 130c to be the second zone.

Thereafter, the multi-zone temperature control device 1 may be configured to execute continuous temperature adjustment (the first temperature control procedure) to the first zone, and simultaneously execute continuous temperature adjustment (the second temperature control procedure) to the second zone.

In the first temperature control procedure, the thermo-conductive reservoir 130a and the thermo-conductive reservoir 130b are simultaneously heated and cooled, and kept with the same temperature condition.

In the second temperature control procedure, the thermo-conductive reservoir 130c is independent from the thermo-conductive reservoir 130a and the thermo-conductive reservoir 130b, and heated and cooled independently.

As a result, the disclosure may be used to simultaneously execute two sets of temperature control procedures through two-zone independent temperature adjustment.

In some other embodiments, the inspector may set the thermo-conductive reservoir 130a to be the first zone, set the thermo-conductive reservoir 130b to be the second zone, set the thermo-conductive reservoir 130c to be the third zone, and execute independent continuous temperature adjustment to three zones to make the three thermo-conductive reservoirs 130a-130c be heated and cooled independently.

As a result, the disclosure may be used to simultaneously execute three sets of temperature control procedures through three-zone independent temperature adjustment.

Further, the numbers of the thermostat 121, the adjustment block 120, and the thermo-conductive reservoir 130 as shown in the figures of the disclosure are solely exemplary, and the numbers of the thermostat 121, the adjustment block 120, and the thermo-conductive reservoir 130 of the disclosure are not limited thereto. The numbers of the thermostat 121, the adjustment block 120, and the thermo-conductive reservoir 130 may be arbitrarily modified according to the inspection requirement on the basis of the disclosure.

In some embodiments, the number of thermostat 121 and the number of the adjustment block 120 may be the same or different, here is not intended to be limiting.

In some embodiments, when the number of thermostat 121 and the number of the adjustment block 120 are the same, the thermostats 121 and the adjustment blocks 120 are arranged one by one. That is, the temperature adjustment (heating or cooling) of each adjustment block 120 is performed by exclusive thermostat 121.

In some embodiments, when the number of thermostat 121 is more than the number of the adjustment block 120, the temperature adjustment of at least one adjustment block 120 may be simultaneously performed by a plurality of thermostats 121 to increase the temperature adjustment efficiency.

In some embodiments, when the number of thermostat 121 is less than the number of the adjustment block 120, at least one thermostat 121 is used to simultaneously or time-dividingly perform the temperature adjustment to a plurality of adjustment blocks 120. The adjustment blocks 120 may be corresponding to the thermo-conductive reservoirs 130 in the same zone or different zones, here is not intended to be limiting. As a result, the arrangement may reduce the number of the thermostat 121, and further reduce the hardware cost and device volume.

In some embodiment, the number of the adjustment block 120 and the number of the thermo-conductive reservoir 130 may be the same or different, here is not intended to be limiting.

In some embodiments, when the number of the adjustment block 120 and the number of the thermo-conductive reservoir 130 are the same, the adjustment block 120 and the thermo-conductive reservoir 130 may be arranged one by one. That is, the temperature adjustment of each thermo-conductive reservoir 130 may be performed through using the exclusive adjustment block 120 contact thereto.

In some embodiments, when the number of the adjustment block 120 is more than the number of the thermo-conductive reservoir 130, the temperature adjustment of at least one thermo-conductive reservoir 130 may be performed through using multiple adjustment blocks 120 simultaneously contact thereto to increase the temperature adjustment efficiency. In some embodiments, the adjustment blocks 120 may contact the thermo-conductive reservoir 130 from different directions.

Taking two adjustment blocks 120 as an example, the contact positions of those with the thermo-conductive reservoir 130 may be distanced by 180 degrees.

Taking three adjustment blocks 120 as an example, the contact positions of those with the thermo-conductive reservoir 130 may be distanced by 60 degrees.

In some embodiments, each thermo-conductive reservoir 130 in the same zone is corresponding to the same number of the adjustment block 120 to ensure that each thermo-conductive reservoir 130 in the same zone has the same temperature adjustment efficiency.

In some embodiments, when the number of the adjustment block 120 is less than the number of the thermo-conductive reservoir 130, at least one adjustment block 120 is used to simultaneously or time-dividingly perform the temperature adjustment to a plurality of thermo-conductive reservoirs 130. The adjustment blocks 120 may be corresponding to the thermo-conductive reservoirs 130 in the same zone or different zones, here is not intended to be limiting. As a result, the arrangement may reduce the number of adjustment block 120, and further reduce the hardware cost and device volume.

Figure 10:
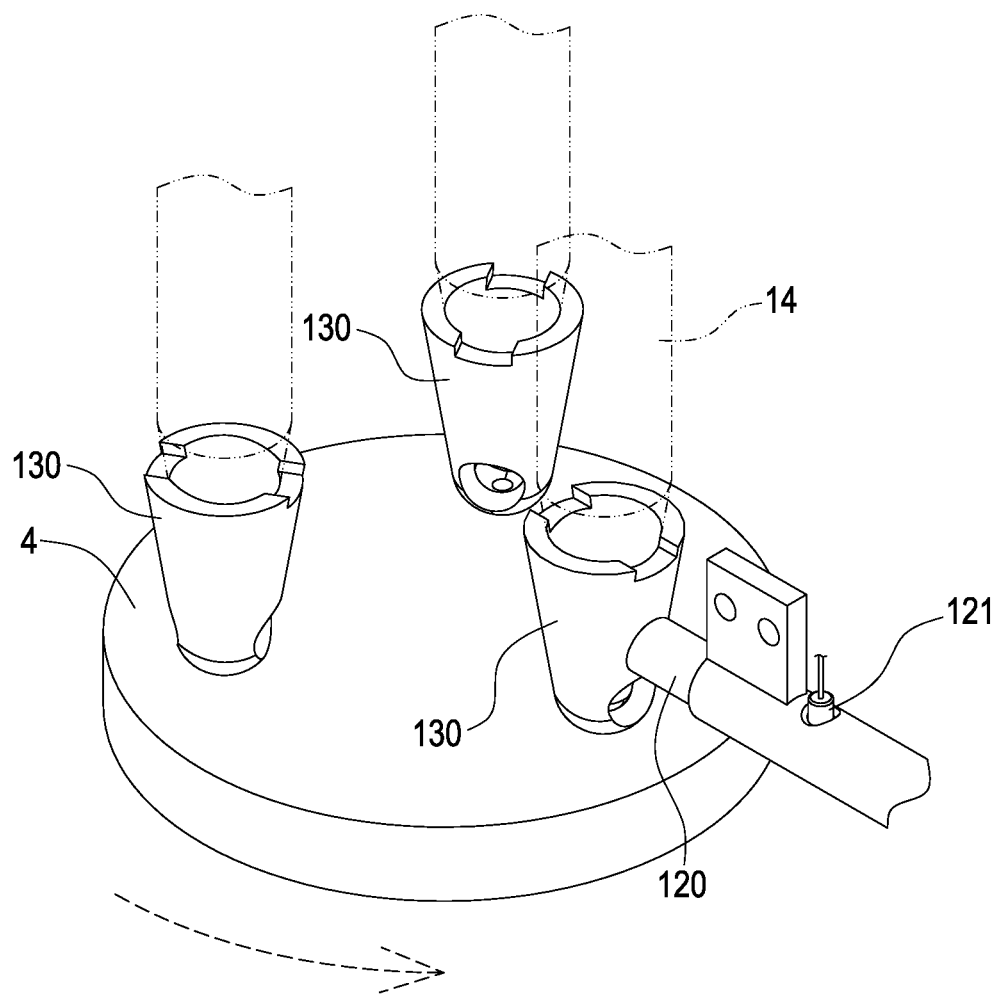
FIG. 10 is a heating schematic diagram of the multi-zone temperature control device of the disclosure in accordance with some other embodiments.

Please refer to FIG. 10, which is a heating schematic diagram of the multi-zone temperature control device of the disclosure in accordance with some other embodiments. In the embodiment of FIG. 10, the thermo-conductive reservoirs 130 are disposed circularly, for example, disposed on the rotational plate 4. The adjustment blocks 120 are fixedly disposed and surround the rotational plate 4. When the thermo-conductive reservoir 130 is rotated to the heating position of designated adjustment block 120, the control device 10 may control the designated adjustment block 120 to contact the thermo-conductive reservoir 130 to perform the temperature adjustment.

Figure 11:
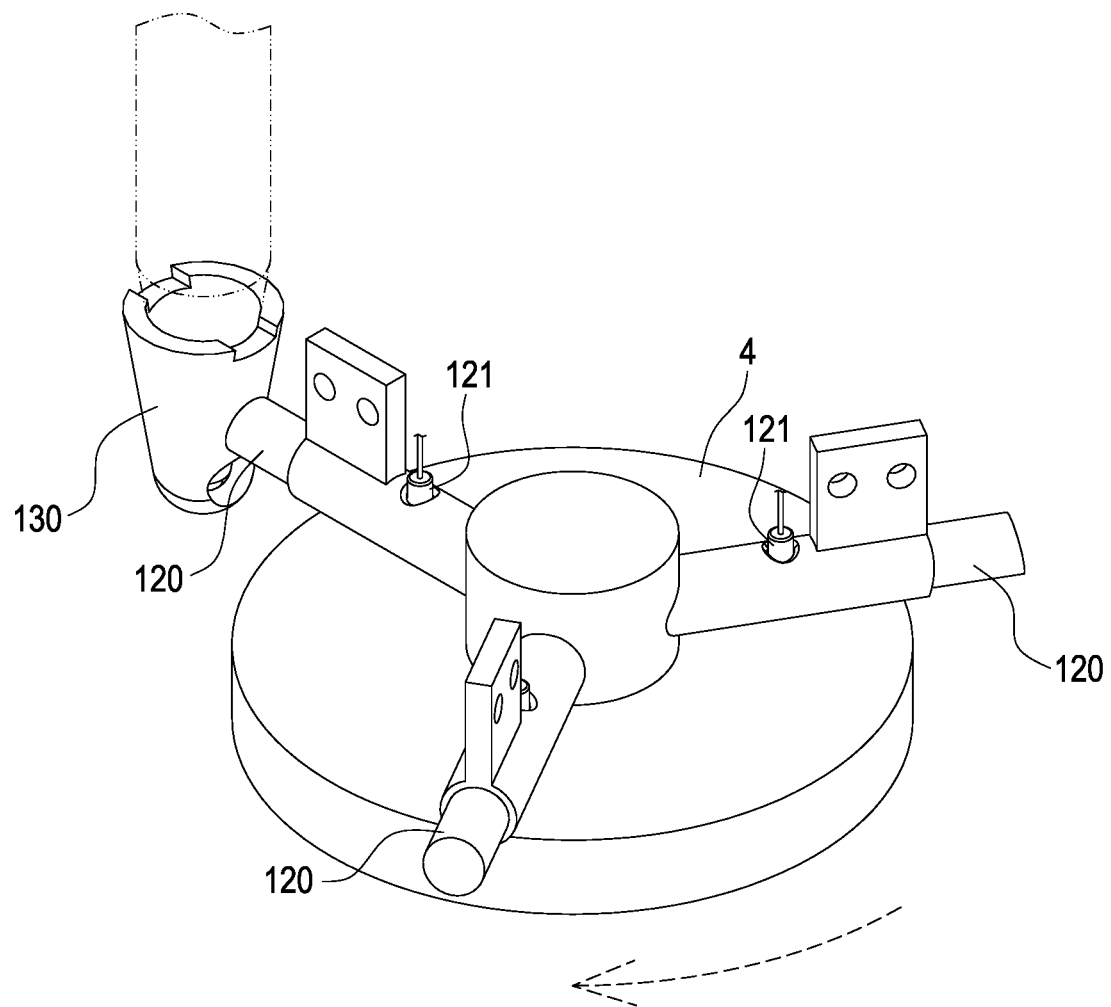
FIG. 11 is a heating schematic diagram of the multi-zone temperature control device of the disclosure in accordance with some other embodiments.

Please refer to FIG. 11, which is a heating schematic diagram of the multi-zone temperature control device of the disclosure in accordance with some other embodiments. In the embodiment of FIG. 11, the adjustment blocks 120 are disposed circularly, for example, disposed on the rotational plate 4. The thermo-conductive reservoirs 130 are fixedly disposed and surround the rotational plate 4. When the adjustment blocks 1200 is rotated to face designated thermo-conductive reservoir 130, the control device 10 may control the adjustment block 120 to contact the thermo-conductive reservoir 130 to perform the temperature adjustment. Therefore, the thermo-conductive reservoir 130 does not need to be moved to prevent the specimen from spilling over due to movement.

Figure 3:
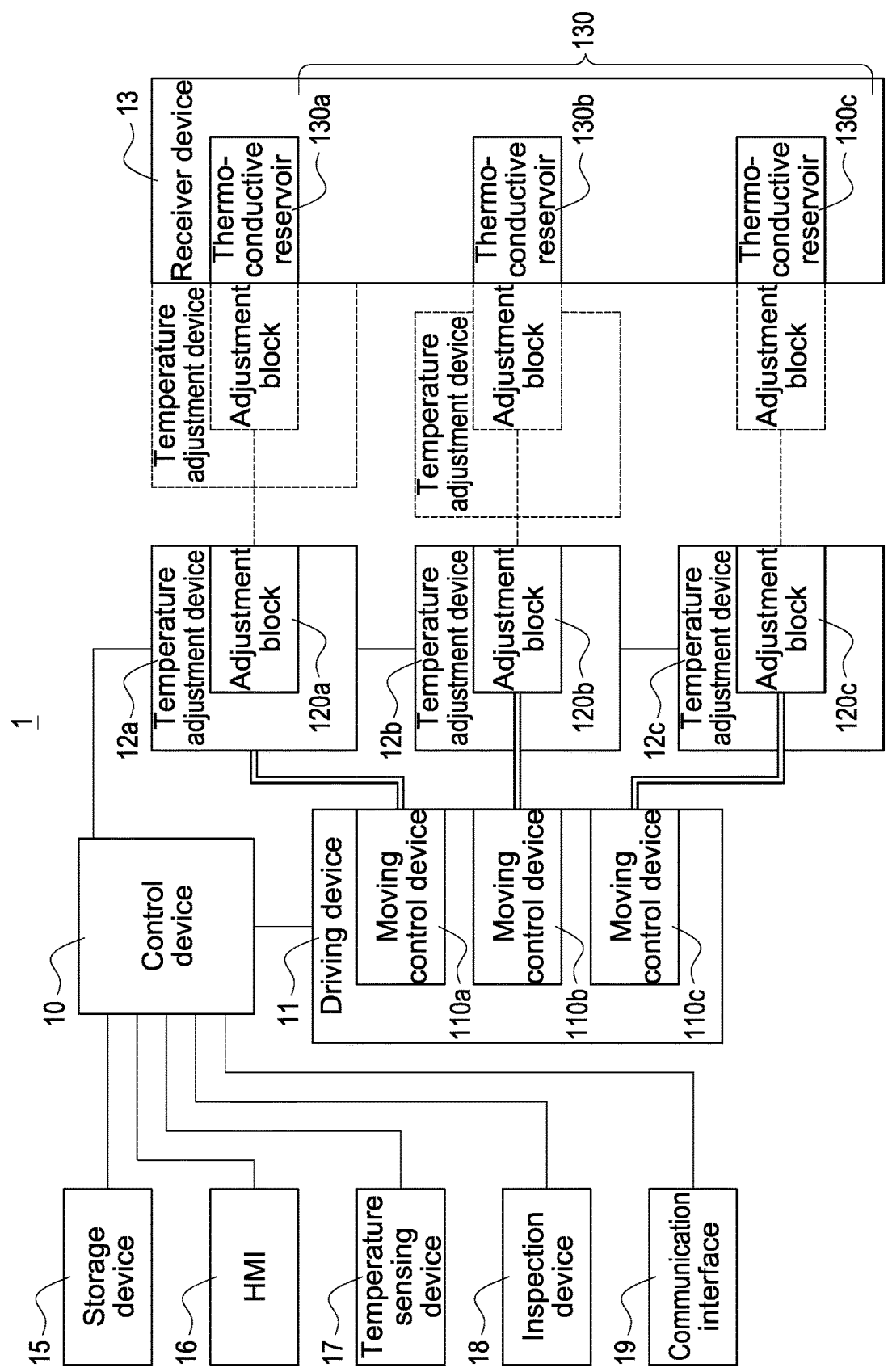
FIG. 3 is an architecture diagram of a multi-zone temperature control device of the disclosure in accordance with some embodiments.

Please refer to FIG. 1 to FIG. 3, FIG. 3 is an architecture diagram of a multi-zone temperature control device of the disclosure in accordance with some embodiments.

In some embodiments, the driving device 11 may include a plurality of moving control devices (three moving control devices 110a-110c are shown in FIG. 3 as an example).

The moving control devices 110a-110c are used to control the contact statuses between the adjustment blocks 120a-120c and the thermo-conductive reservoirs 130a-130c, that is, to control each adjustment block 120a-120c contact or leave corresponding thermo-conductive reservoir 130a-130c.

In some embodiments, the multi-zone temperature control device 1 may include a storage device 15.

The storage device 15 may include a flash memory, a solid state drive, a hard disk drive, a RAM, a ROM, an EEPROM, and/or the other storage devices.

In some embodiments, the multi-zone temperature control device 1 may include a human-machine interface (HMI) 16.

The HMI 16 may include an output interface and an input interface. The input interface may include a button, a keyboard, a mouse, a touch pad, and/or the other input devices. The output interface may include a display, a speaker, a printer, and/or the other output devices.

In some embodiments, the multi-zone temperature control device 1 may include a temperature sensing device 17, for example, a thermocouple thermometer, an infrared thermometer, or the other types of thermometer.

The temperature sensing device 17 is electrically connected to the control device 10, and used to sense the temperature of each thermo-conductive reservoir 130, and may also be used to sense the temperature of the specimen 140 or the test tube 14.

In some embodiments, the multi-zone temperature control device 1 may include an inspection device 18.

The inspection device 18 is electrically connected to the control device 10, and used to inspect the specimen inside the test tube in the thermo-conductive reservoir 130 to generate the inspection result.

In some embodiments, the inspection device 18 may be an optical inspection device, and used to inspect the fluorescent label in the specimen.

In some embodiments, the inspection device 18 may include an excitation light element and a sensing optical element.

The excitation light element is used to emit the excitation light to the specimen to induce the fluorescence. The sensing optical element is used to sense the fluorescent label of the specimen.

Specifically, the inspector may add the fluorescein dye into the specimen to dye the inspection target (for example, virus). Afterward, the inspection target is made to continuously self-replicate by repeatedly executing the temperature control procedure until the fluorescent label is detected. That is, the number of the inspection target is enough to be detected.

In some embodiments, the multi-zone temperature control device 1 may include a communication interface 19.

The communication interface 19 may include a wireless communication module and/or a wired communication module. The wireless communication module may be, for example, a Wi-Fi module, a Bluetooth module, a cellular network module, and/or the other wireless communication modules. The wired communication module may be, for example, an ethernet module, a powerline network module, a serial line module, and/or the other wired communication modules.

Please refer to FIG. 4, in some embodiments, the test tube 14 may be a deformable plastic thin bag, and used to accommodate the specimen 140. When the inspector put the test tube 14 in the thermo-conductive reservoir 130, the inspector may squeeze the test tube 14 downward in a direction toward the thermo-conductive reservoir 130 to make the test tube 14 be deformed in the thermo-conductive reservoir 130 and closely attach to the inner wall of the thermo-conductive reservoir 130, thereby increasing the thermo-conductive efficiency.

In some embodiments, the thermo-conductive reservoir 130 is, for example, a metal thin cup. The test tube 14 is a plastic hard tube, and has a diameter slightly greater than that of the thermo-conductive reservoir 130.

When the inspector put the test tube 14 into the thermo-conductive reservoir 130, the test tube 14 squeeze the thermo-conductive reservoir 130 to make the thermo-conductive reservoir 130 temporarily deformative to attach the test tube 14, thereby increasing the thermo-conductive efficiency.

In some embodiments, the thermo-conductive reservoir 130 may be formed with one or multiple through holes 131, 132 used to arrange one or multiple optical fiber cables.

Moreover, one optical fiber cable (emission optical fiber cable) is connected with the excitation light element and passes through the through hole 131. The other optical fiber cable (sensing optical fiber cable) is connected with the sensing optical element and passes through the through hole 132.

As a result, the excitation light element may emit the excitation light to the specimen 140 in the test tube 14 through the emission optical fiber cable. The sensing optical element may sense the fluorescent label of the specimen 140 through the sensing optical fiber cable.

In some embodiments, the temperature adjustment device 12 includes the adjustment block 120, the thermostat 121, and the movable component 122.

In some embodiments, the movable component 122 is telescoping structure, the adjustment block 120 is disposed on the front end of the movable component 122 and the driving device 11 is connected to the back end of the movable component 122.

Further, the adjustment block 120 may be wholly or partially retracted into the movable component 122, and perform heating/cooling through the thermostat 121 disposed in the movable component 122.

Moreover, when the adjustment block 120 is retracted in the movable component 122, the adjustment block 120 does not contact the thermo-conductive reservoir 130.

In some embodiments, when the driving device 11 is pneumatic power device, the movable component 122 may be a telescopic tube structure. When the moving control device is activated and the high-pressure gas is supplied into the movable component 122, the high-pressure gas may push out the adjustment block 120 to make the adjustment block 120 contact the thermo-conductive reservoir 130.

In some embodiments, when the driving device 11 is a motor power device, the movable component 122 may be a spiral telescopic tube structure. When the moving control device is activated, the motor may rotate the movable component 122 and/or the adjustment block 120 through the transmission part to push out the adjustment block 120 to make the adjustment block 120 contact the thermo-conductive reservoir 130.

In some embodiments, the thermostat 121 and the temperature sensing device 17 may be disposed in the movable component 122.

In some embodiments, the contact surface of the adjustment block 120 used for contacting the thermo-conductive reservoir 130 is an inclined surface.

In some embodiments, the contact surface of the adjustment block 120 is formed with a concave for attaching the outer arc of the thermo-conductive reservoir 130.

In some embodiments, the concave may be attached with a thermo-conductive buffering patch, for example, the thermal pad, used for eliminating the deviation between the concave of the contact surface and the outer arc of the thermo-conductive reservoir 130.

Figure 5:
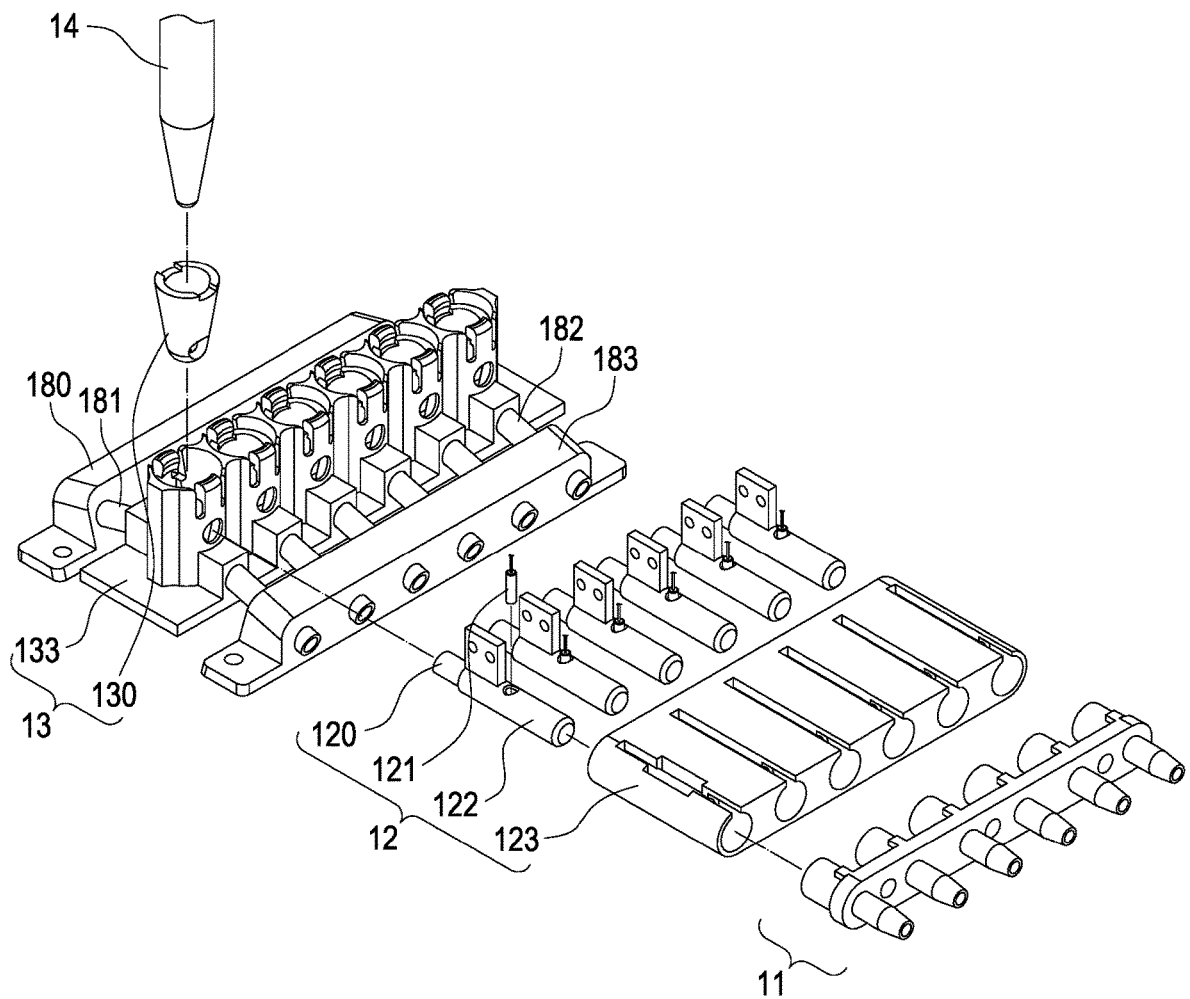
FIG. 5 is a schematic diagram of partial exterior of the multi-zone temperature control device of the disclosure in accordance with some embodiments.
Figure 6:
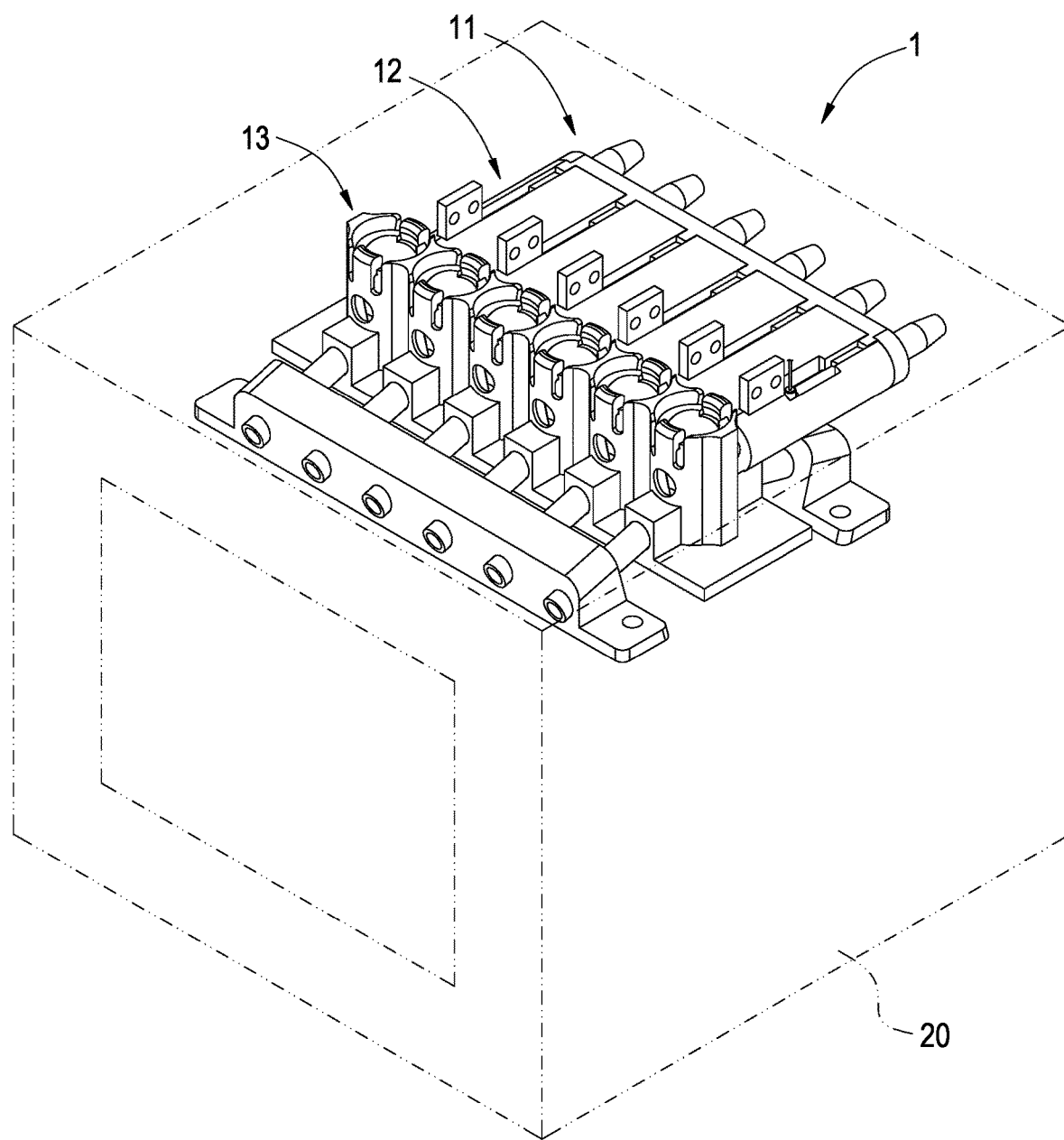
FIG. 6 is a schematic diagram of exterior of the multi-zone temperature control device of the disclosure in accordance with some embodiments.
Figure 7:
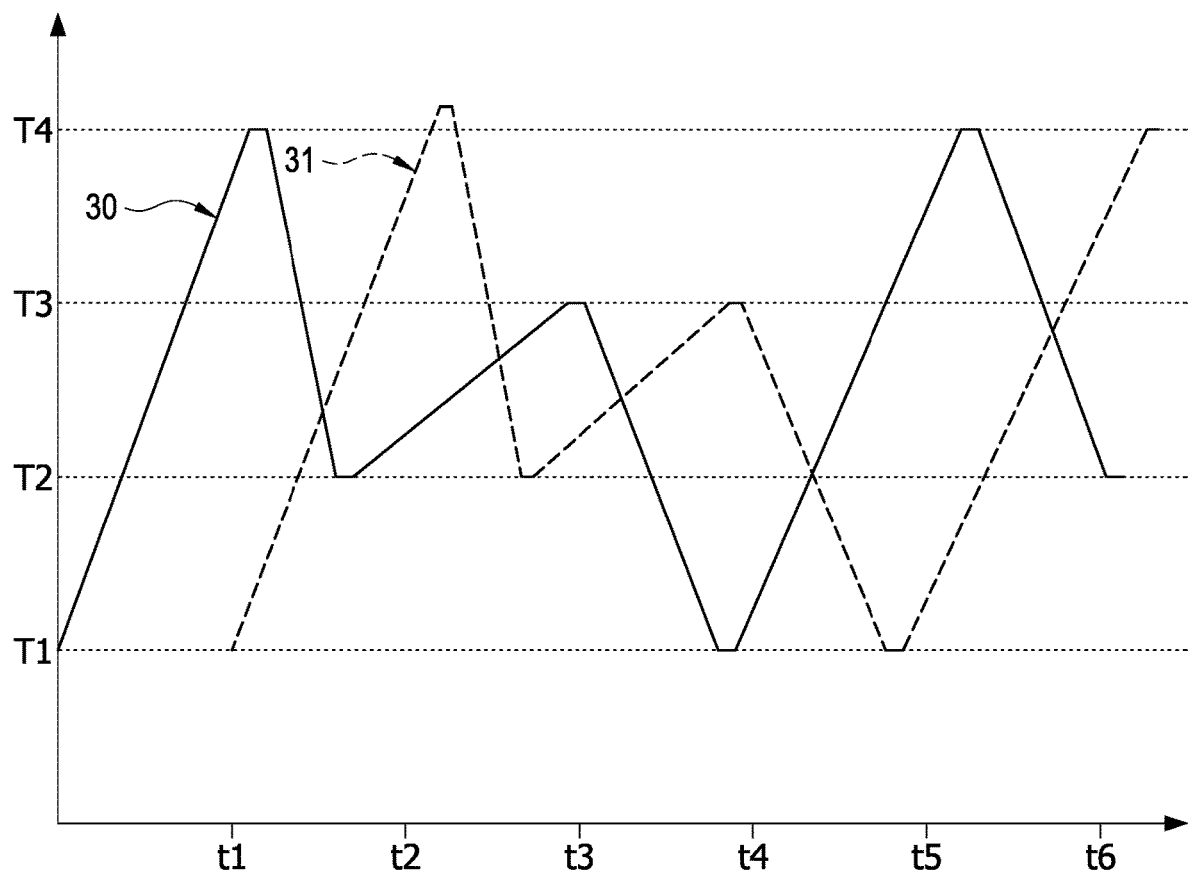
FIG. 7 is a temperature change curve diagram of a multiple temperature control procedures of the disclosure in accordance with some embodiments.
Figure 8:
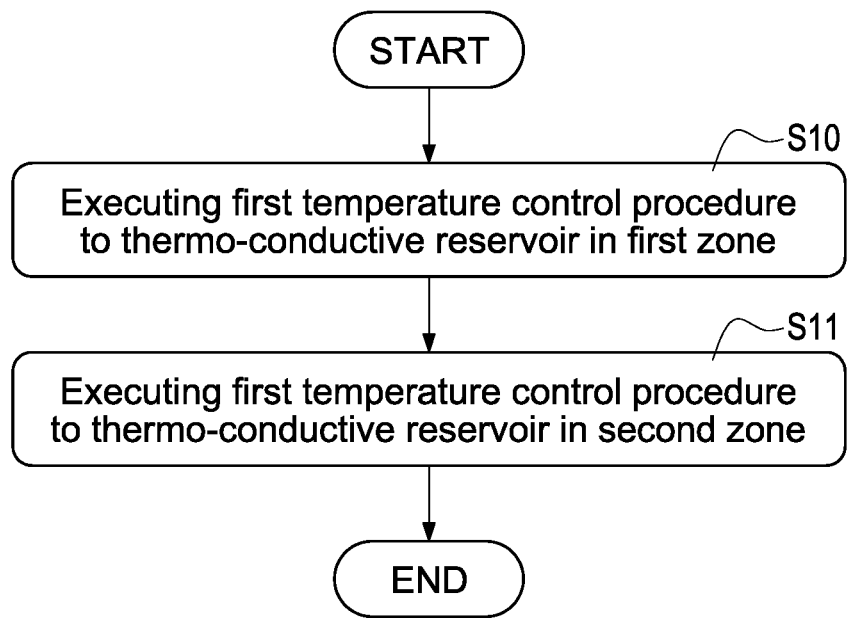
FIG. 8 is a flowchart of a temperature control method of the disclosure in accordance with some embodiments.
Figure 9:
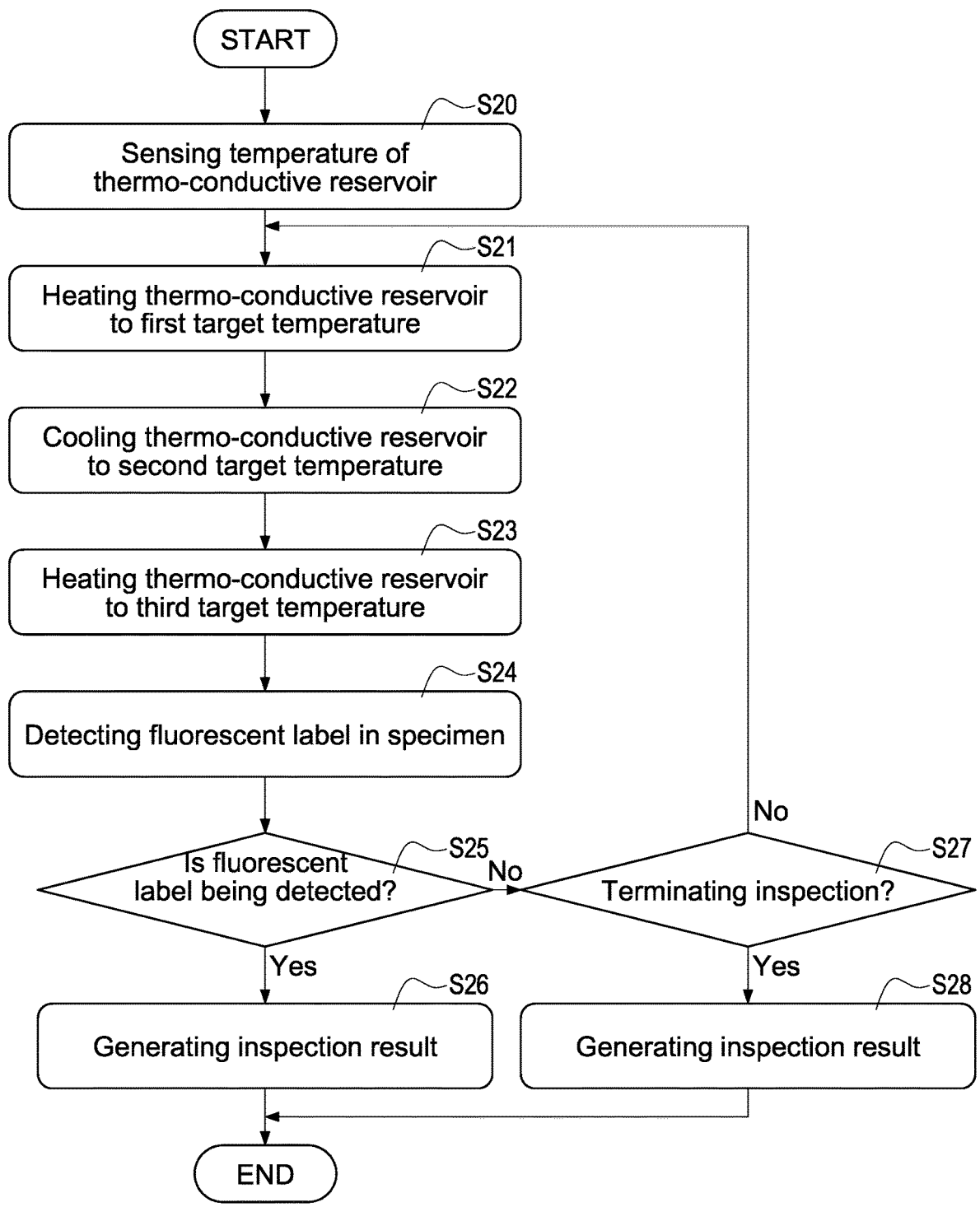
FIG. 9 is a flowchart of a temperature control procedure of the disclosure in accordance with some embodiments.

Please refer to FIG. 5, FIG. 5 is a schematic diagram of partial exterior of the multi-zone temperature control device of the disclosure in accordance with some embodiments.

In some embodiments, the driving device 11 is the pneumatic power device, and may include a plurality of gas pipelines. The gas pipelines are respectively connected to the pneumatic driver through a plurality of moving control devices. The pneumatic driver may be, for example, an independent pneumatic cylinder, and used to provide the high-pressure gas to the gas pipelines.

In some embodiments, the moving control devices may be a plurality of electromagnetic valves. When the electromagnetic valve is activated, the high-pressure gas is introduced into the movable component 122 from corresponding gas pipeline to push the movable component 122 to move the adjustment 120 to contact corresponding thermo-conductive reservoir 130.

In some embodiments, the movable component 122 may be a spring device with a spring disposed therein. The moving control devices may be the buckle devices.

When the buckle is released, the adjustment block 120 may be moved to contact corresponding thermo-conductive reservoir 130 through the restoring force from the spring.

In some embodiments, the temperature adjustment device 11 may include a thermal insulation cover 123. The thermal insulation cover 123 is used to wholly or partially cover the movable component 122 or the adjustment block 120 to thermally insulate the adjustment block 120.

In some embodiments, the thermal insulation cover 123 is made of thermal insulation material, for example, the material with low-thermal conductivity such as foam, glass fiber, etc.

In some embodiments, the receiver module 13 may include a fixation base 133. The fixation base 133 is used for fixedly arranging a plurality of thermo-conductive reservoirs 130, and is made of low-thermal conductivity material, for example, BAKELITE™ synthetic resin or glass fiber.

In some embodiments, the fixation base 133 may be formed with a hook used for fixing the thermo-conductive reservoirs 130.

In some embodiments, the fixation base 133 is formed with a plurality of openings thereon. The adjustment blocks 120 pass through the openings to contact corresponding thermo-conductive reservoirs 130.

In some embodiments, the inspection device 18 may include a plurality of optical fiber fixation bases 180, 183, a plurality of optical fiber cables 181 (emission optical fiber cables), and a plurality of optical fiber cables 182 (sensing optical fiber cables).

The optical fiber cables 181 connected to the excitation light element pass through the optical fiber fixation base 180 and are inserted into the opening on one side of the fixation base 133.

The optical fiber cables 182 connected to the sensing optical element pass through the optical fiber fixation base 183 and are inserted into the opening on another side of the fixation base 133.

Please refer to FIG. 1 to FIG. 6, FIG. 6 is a schematic diagram of exterior of the multi-zone temperature control device of the disclosure in accordance with some embodiments.

In some embodiments, the multi-zone temperature control device 1 is a point of care testing (POCT) device.

The devices of the multi-zone temperature control device 1, for example, the driving device 11, the temperature adjustment device 11, and the receiver device 13, are disposed in the housing 20 to facilitate carrying and moving.

As a result, the disclosure may be used in the home environment or mobile inspection station.

Please refer to FIG. 1 to FIG. 6 and FIG. 8, FIG. 8 is a flowchart of a temperature control method of the disclosure in accordance with some embodiments.

The temperature control method in the embodiments of the disclosure may be realized by the multi-zone temperature control device 1 in any aforementioned embodiments.

In some embodiments, the storage device 15 may include a non-transitory computer readable record medium. The non-transitory computer readable record medium is configured to store a computer program (such as firmware or application program), and the computer program records the computer executable code. When the control device 10 executes the code, the control device 10 may execute the steps of the temperature control method in the after-mentioned embodiments.

In some embodiments, taking two sets of temperature control procedures being simultaneously executed with respect to two zones as an example, however, the numbers of zone and temperature control procedure being simultaneously executed are not limited thereto.

In the step S10, the control device 10 is configured to execute the first temperature control procedure to the thermo-conductive reservoir 130 in the first zone to control the temperature adjustment device 12 (first temperature adjustment device) in the first zone to adjust the temperature of the adjustment block 120 (first adjustment block) in the first zone, and control the driving device 11 to adjust the first contact status between the first adjustment block and the thermo-conductive reservoir 130 (first thermo-conductive reservoir) in the first zone to make the first thermo-conductive reservoir reach a plurality of target temperatures of the first temperature control procedure sequentially.

In the step S11, at the same time of executing the first temperature control procedure, the control device 10 is configured to execute the second temperature control procedure to control the temperature adjustment device 12 (second temperature adjustment device) in the second zone to adjust the temperature of the adjustment block 120 (second adjustment block) in the first zone, and control the driving device 11 to adjust the second contact status between the second adjustment block and the thermo-conductive reservoir 130 (second thermo-conductive reservoir) in the second zone to make the second thermo-conductive reservoir reach a plurality of target temperatures of the second temperature control procedure sequentially.

As a result, the disclosure may be used to simultaneously perform the temperature change control to multiple groups of specimens through independently executing corresponding temperature control procedures to the thermo-conductive reservoirs of multiple zones.

Please refer to FIG. 1 to FIG. 6 and FIG. 8 to FIG. 9, FIG. 9 is a flowchart of a temperature control procedure of the disclosure in accordance with some embodiments.

The temperature control procedures (for example, the first temperature control procedure and the second temperature control procedure) of the disclosure may include the following steps S20 to S28.

In the step S20, the control device 10 is configured to continuously sense the temperatures of the thermo-conductive reservoirs 130 through the temperature sensing device 17.

In the step S21, the control device 10 is configured to control the temperature adjustment device 12 to heat the adjustment block 120, and control the driving device 11 to make the heated adjustment block 120 contact the thermo-conductive reservoir 130 in the corresponding zone to heat the thermo-conductive reservoir 130 to the first target temperature.

In the step S22, the control device 10 is configured to control the driving device 11 to make the adjustment block 120 leave the thermo-conductive reservoir 130 to cool the thermo-conductive reservoir 130 to the second target temperature.

In the step S23, the control device 10 is configured to control the temperature adjustment device 12 to re-heat the adjustment block 120, and control the driving device 11 to make the adjustment block 120 contact the thermo-conductive reservoir 130 in the corresponding zone to heat the thermo-conductive reservoir 130 to the third target temperature.

In some embodiments, the first target temperature, the second target temperature, and the third target temperature are different.

In some embodiments, the first target temperature may be greater than the third target temperature.

In some embodiments, the third target temperature may be greater than or equal to the second target temperature.

In the step S24, the control device 10 is configured to inspect the specimen 140 inside the test tube 14 disposed in the thermo-conductive reservoir 130 through the inspection device 18 (for example, the optical inspection device) to detect the fluorescent label in the specimen 140.

In the step S25, the control device 10 is configured to determine whether the fluorescent label in the specimen 140 is detected.

If the fluorescent label is detected, the step S26 is executed. The control device 10 generates the inspection result.

In some embodiments, the control device 10 may be configured to determine the cycle threshold value (CT) as the inspection result according to presently executed temperature cycle times (that is, the execution times of the temperature control procedure).

If the fluorescent label is not being detected, the step S27 is executed. The control device 10 is configured to determine whether to terminate the inspection. For example, whether the execution times of the temperature control procedure are greater than the predetermined stopping time, or the inspector terminate the inspection manually.

If the control device 10 determines that the inspection does not need to be terminated, the step S21 is re-executed to re-execute the temperature control procedure.

The thermo-conductive reservoirs 130 are repeatedly made to reach the target temperatures of the temperature control procedure sequentially until the fluorescent label is detected or the inspection is terminated.

If the control device 10 determines that the inspection needs to be terminated, in the step S28, the control device 10 generates the inspection result. The inspection result may be that, for example, the inspection target (for example, virus) is undetected.

Please refer to FIG. 1 to FIG. 7, FIG. 7 is a temperature change curve diagram of a multiple temperature control procedures of the disclosure in accordance with some embodiments.

In some embodiments, the thermostat 121 may be a heater, and used to heat the adjustment block 120.

Further, the first temperature control procedure and the second temperature control procedure may be the same temperature control procedure, the difference is that the execution time point is different.

The first temperature control procedure and the second temperature control procedure are the temperature control procedure of PCR, and sequentially execute the temperature cycle of DNA denaturing (90° C.-96° C.), annealing (25° C.-65° C.), and extending (70° C.-75° C.). The DNA content may be increased through repeatedly executing the temperature cycle to generate the inspection result of the specimen.

Specifically, the control device 10 begins to execute the first temperature control procedure to the thermo-conductive reservoir 130 in the first zone to make the thermo-conductive reservoir 130 (the first thermo-conductive reservoir) in the first zone be heated from temperature T1 to temperature T4 (the first target temperature, for example, 90° C.) at time point t1 through making the adjustment block 120 contact the first thermo-conductive reservoir.

Thereafter, the first thermo-conductive reservoir is made to be cooled from temperature T4 to temperature T2 (the second target temperature, for example, 25° C.) at time point t2 through making the adjustment block 120 leave the thermo-conductive reservoir 130 in the first zone.

Afterward, the thermo-conductive reservoir 130 in the first zone is made to be heated from temperature T2 to temperature T3 (the third target temperature, for example, 70° C.) at time point t3 through making the adjustment block 120 contact the thermo-conductive reservoir 130 in the first zone.

At the end, the first thermo-conductive reservoir made to be cooled from temperature T3 to temperature T1 at time point t4 through making the adjustment block 120 leave the thermo-conductive reservoir 130 in the first zone to complete the temperature cycle of first time.

The first zone temperature curve 30 is the result obtained from repeating the temperature cycle to the thermo-conductive reservoir 130 in the first zone.

Further, at time point t2, the control device 10 begins to execute the second temperature control procedure to the thermo-conductive reservoir 130 in the second zone to obtain the result as the second zone temperature curve 31.

Therefore, the disclosure may realize the execution of the temperature control procedures in a time-sharing manner to the thermo-conductive reservoirs in different zones.

While this disclosure has been described by means of specific embodiments, numerous modifications and variations may be made thereto by those skilled in the art without departing from the scope and spirit of this disclosure set forth in the claims.

What is claimed is:

1. A multi-zone temperature control device, comprising:
  a receiver device comprising a plurality of thermo-conductive reservoirs, each of the thermo-conductive reservoirs configured to contain a test tube accommodating an individual specimen, wherein one of the thermo-conductive reservoirs belongs to a first zone and another one of the thermo-conductive reservoirs belongs to a second zone, wherein each of the thermo-conductive reservoirs has an opening disposed thereon;
  a plurality of temperature adjustment devices, configured to adjust temperatures of a plurality of adjustment blocks, and contact the thermo-conductive reservoir of the first zone through one of the adjustment blocks to adjust temperature of the thermo-conductive reservoir of the first zone and contact the thermo-conductive reservoir of the second zone through another one of the adjustment blocks to adjust temperature of the thermo-conductive reservoir of the second zone, wherein each of the adjustment blocks is controlled to insert into each corresponding one of the thermo-conductive reservoirs through the opening to simultaneously contact the thermo-conductive reservoir and the test tube disposed in the thermo-conductive reservoir;
  a driving device, configured to change a contact status between the one of the adjustment blocks and the thermo-conductive reservoir of the first zone and the another one of the adjustment blocks and the thermo-conductive reservoir of the second zone; and
  a control device, electrically connected with the driving device and the temperature adjustment devices, and configured to execute a first temperature control procedure to control one of the temperature adjustment devices to adjust temperature, and control the driving device to change the contact status between the one of the adjustment blocks and the thermo-conductive reservoir in the first zone to make the thermo-conductive reservoir in the first zone reach a plurality of target temperatures of the first temperature control procedure sequentially, and configured to execute a second temperature control procedure to control one of the temperature adjustment devices to adjust temperature, and control the driving device to change the contact status between the another one of the adjustment blocks and the thermo-conductive reservoir in the second zone to make the thermo-conductive reservoir in the second zone reach a plurality of target temperatures of the second temperature control procedure sequentially.

2. The multi-zone temperature control device according to claim 1, further comprising: a temperature sensing device, electrically connected to the control device and configured to sense a temperature of each thermo-conductive reservoir.

3. The multi-zone temperature control device according to claim 1, wherein each of the thermo-conductive reservoirs comprises two through holes configured to be disposed with two optical fibers; and
  an excitation light element is configured to emit an excitation light to one of the optical fibers, and a sensing optical element is configured to sense a fluorescent label through another one of the optical fibers.

4. The multi-zone temperature control device according to claim 1, wherein the driving device comprises a plurality of moving control devices, each of the plurality of moving control devices is configured to respectively make one of the adjustment blocks contact or leave a corresponding one of the thermo-conductive reservoirs.

5. The multi-zone temperature control device according to claim 4, wherein the driving device further comprises:
  a plurality of gas pipelines, respectively connected with the moving control devices; and
  a pressure driver, configured to provide a high-pressure gas to the gas pipelines;
  wherein the moving control devices are a plurality of electromagnetic valves, and each individual moving control device is connected to a corresponding one of the adjustment blocks through a movable component, and configured to introduce the high-pressure gas, when being activated, to push the movable component to move the adjustment block to contact a corresponding one of the thermo-conductive reservoir.

6. The multi-zone temperature control device according to claim 1, wherein each temperature adjustment device comprises a thermostat, configured to heat the adjustment block;
  wherein the driving device comprises a plurality of movable components, the driving device is connected to a back end of at least one of the movable components and one of the adjustment blocks is disposed on a front end of the at least one of the movable components;
  wherein the thermostat is disposed on one of the movable components.

7. The multi-zone temperature control device according to claim 6, wherein a contact surface of each adjustment block contacting each thermo-conductive reservoir is an inclined surface;
wherein the temperature adjustment device comprises a thermal insulation cover, configured to partially cover the movable components; and
wherein the thermal insulation cover comprises foam or glass fiber.

8. The multi-zone temperature control device according to claim 1, wherein the thermo-conductive reservoirs comprise a thin metal cup with a high-thermal conductivity which is greater than or equal to 200 W/m*K, and a thickness thereof is less than or equal to 0.5 mm.

9. The multi-zone temperature control device according to claim 1, wherein the receiver device comprises a fixation base made of BAKELITE™ synthetic resin or glass fiber and configured to fix the thermo-conductive reservoirs.

10. The multi-zone temperature control device according to claim 9, wherein the fixation base comprises a plurality of openings, configured for the adjustment blocks passing therethrough to contact the thermo-conductive reservoirs.

11. The multi-zone temperature control device according to claim 1, wherein the multi-zone temperature control device is a point of care testing (POCT) device.

12. The multi-zone temperature control device according to claim 1, wherein the temperature adjustment devices comprise a plurality of heaters, configured to heat the adjustment blocks;
the control device is configured to execute the first temperature control procedure to make the thermo-conductive reservoir in the first zone be heated to a first target temperature, cooled to a second target temperature, and heated to a third target temperature by making the one of the adjustment blocks contact and leave the thermo-conductive reservoir in the first zone, wherein the first target temperature, the second target temperature, and the third target temperature are different.

13. The multi-zone temperature control device according to claim 12, wherein the control device is configured to execute the first temperature control procedure until a terminating inspection condition is satisfied.

14. A multi-zone temperature control method, comprising steps of:
a) executing a first temperature control procedure to control a first temperature adjustment device to adjust temperature of a first adjustment block, and control a driving device to adjust a first contact status between the first adjustment block and a first thermo-conductive reservoir to make the first thermo-conductive reservoir reach a plurality of target temperatures of the first temperature control procedure sequentially, wherein the first thermo-conductive reservoir contains a first test tube accommodating a first specimen and has a first opening disposed thereon, and the first adjustment block is controlled to insert into the first thermo-conductive reservoir through the first opening to simultaneously contact the first thermo-conductive reservoir and the first test tube disposed in the first thermo-conductive reservoir; and b) at a same time of executing the first temperature control procedure, executing a second temperature control procedure to control a second temperature adjustment device to adjust temperature of a second adjustment block, and control the driving device to adjust a second contact status between the second adjustment block and a second thermo-conductive reservoir to make the second thermo-conductive reservoir reach a plurality of target temperatures of the second temperature control procedure sequentially, wherein the second thermo-conductive reservoir contains a second test tube accommodating a second specimen and has a second opening disposed thereon, and the second adjustment block is controlled to insert into the second thermo-conductive reservoir through the second opening to simultaneously contact the second thermo-conductive reservoir and the second test tube disposed in the second thermo-conductive reservoir.

15. The multi-zone temperature control device according to claim 14, wherein the a) further comprises steps of:
a1) controlling the first temperature adjustment device to heat the first adjustment block, and controlling the driving device to make the first adjustment block contact the first thermo-conductive reservoir to heat the first thermo-conductive reservoir to a first target temperature;
a2) controlling the driving device to make the first adjustment block leave the first thermo-conductive reservoir to cool the first thermo-conductive reservoir to a second target temperature; and
a3) controlling the first temperature adjustment device to heat the first adjustment block, and controlling the driving device to make the first adjustment block contact the first thermo-conductive reservoir to heat the first thermo-conductive reservoir to a third target temperature, wherein the first target temperature, the second target temperature, and the third target temperature are different.

16. The multi-zone temperature control device according to claim 14, wherein the a) further comprises a step of:
a4) sensing temperature of the first thermo-conductive reservoir through a temperature sensing device.

17. The multi-zone temperature control device according to claim 14, wherein the a) further comprises a step of:
a5) emitting an excitation light to the first specimen disposed in the first thermo-conductive reservoir through an excitation light element and sensing a fluorescent label in the specimen.

18. The multi-zone temperature control device according to claim 17, wherein the a) further comprises a step of:
a6) repeatedly making the first thermo-conductive reservoir reach the target temperatures of the first temperature control procedure sequentially until the fluorescent label is detected.

* * * * *